(12) United States Patent
McCloskey et al.

(10) Patent No.: US 9,085,542 B1
(45) Date of Patent: Jul. 21, 2015

(54) METHOD FOR SYNTHESIS OF N-METHYL PIPERAZINE DIPHENOLAMIDE AND RELATED COMPOSITION

(71) Applicant: General Electric Company, Schenectady, NY (US)

(72) Inventors: Patrick Joseph McCloskey, Watervliet, NY (US); Julia Lam Lee, Niskayuna, NY (US); Paul Edward Howson, Latham, NY (US); Hongyi Zhou, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 14/303,150

(22) Filed: Jun. 12, 2014

(51) Int. Cl.
*C07D 295/192* (2006.01)

(52) U.S. Cl.
CPC .................................. *C07D 295/192* (2013.01)

(58) Field of Classification Search
CPC .................................................. C07D 295/192
See application file for complete search history.

(56) References Cited

U.S. PATENT DOCUMENTS

| | | | |
|---|---|---|---|
| 2,806,032 A | 9/1957 | Geschickter | |
| 3,470,133 A | 9/1969 | Ohme | |
| 3,876,641 A | 4/1975 | De Muylder | |
| 5,140,068 A | 8/1992 | Siebert et al. | |
| 5,157,077 A | 10/1992 | Siebert et al. | |
| 5,280,068 A | 1/1994 | Siebert et al. | |
| 5,795,702 A | 8/1998 | Tanabe et al. | |
| 6,894,116 B2 | 5/2005 | Lai et al. | |
| 7,985,339 B2 | 7/2011 | Zhang et al. | |
| 8,354,215 B2 | 1/2013 | Yokoi et al. | |
| 2008/0312349 A1 | 12/2008 | Yeager et al. | |

FOREIGN PATENT DOCUMENTS

WO    WO 2010024755 A1 *   3/2010

OTHER PUBLICATIONS

Loginova et al., "Redox-active metal(II) complexes of sterically hindered phenolic ligands: Antibacterial activity and reduction of cytochrome c. Part III. Copper(II) complexes of cycloaminomethyl derivatives of o-diphenols", Polyhedron, Sciencedirect, Jul. 2, 2013, pp. 39-46, vol. 57.

* cited by examiner

*Primary Examiner* — Noble Jarrell
*Assistant Examiner* — John S Kenyon
(74) *Attorney, Agent, or Firm* — Melissa K. Dobson

(57) ABSTRACT

A method for synthesis of N-methyl piperazine diphenolamide is presented. The method includes contacting diphenolic acid with N-methyl piperazine to form a reaction mixture; and heating the reaction mixture to form a reaction product including N-methyl piperazine diphenolamide. An associated composition is also presented.

20 Claims, No Drawings

METHOD FOR SYNTHESIS OF N-METHYL PIPERAZINE DIPHENOLAMIDE AND RELATED COMPOSITION

BACKGROUND

The invention generally relates to method for synthesis of N-methyl piperazine diphenolamide. More particularly, the invention relates to method for one-step synthesis of N-methyl piperazine diphenolamide and related composition.

Typical methods to synthesize N-methyl piperazine diphenolamide include a two-step reaction, which includes converting diphenolic acid to diphenolic acid methyl ester, followed by reaction of the ester with N-methylpiperazine. However, such methods typically require addition of solvents, which necessitates additional steps of solvent removal. Further, this two-step method also requires two separate steps for isolation and purification of the reaction products (diphenolic acid methyl ester and N-methyl piperazine diphenolamide). Therefore, the typical two-step method may not provide the desired efficiency (yield), and may not be cost-effective.

Thus, cost-effective and efficient methods for synthesis of N-methyl piperazine diphenolamide are desired. Further, one-step methods for synthesis of N-methyl piperazine diphenolamide are also desired.

BRIEF DESCRIPTION OF THE INVENTION

Embodiments of the present invention are included to meet these and other needs. One embodiment is a method for synthesis of N-methyl piperazine diphenolamide. The method includes contacting diphenolic acid with N-methyl piperazine to form a reaction mixture; and heating the reaction mixture to form a reaction product including N-methyl piperazine diphenolamide.

One embodiment is a method for synthesis of N-methyl piperazine diphenolamide. The method includes contacting diphenolic acid with N-methyl piperazine under substantially solvent free conditions to form a reaction mixture. The method further includes heating the reaction mixture at a temperature in a range from about 160° C. to about 180° C. for a time duration in a range from about 16 hours to about 40 hours, to form a reaction product including N-methyl piperazine diphenolamide.

One embodiment is a composition including N-methyl piperazine diphenolamide. The composition is formed by contacting diphenolic acid with N-methyl piperazine to form a reaction mixture; and heating the reaction mixture to form a reaction product including the N-methyl piperazine diphenolamide.

DETAILED DESCRIPTION

Approximating language, as used herein throughout the specification and claims, may be applied to modify any quantitative representation that could permissibly vary without resulting in a change in the basic function to which it is related. Accordingly, a value modified by a term or terms, such as "about", and "substantially" is not to be limited to the precise value specified. In some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

In the following specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

A method for synthesis of N-methyl piperazine diphenolamide is presented. In particular, a one-step method for synthesis of N-methyl piperazine diphenolamide is presented. The term "one-step method" as used herein means that the diphenolic acid is directly converted into N-methyl piperazine diphenolamide without the additional intermediate step of forming an ester, as shown in the synthetic scheme 1:

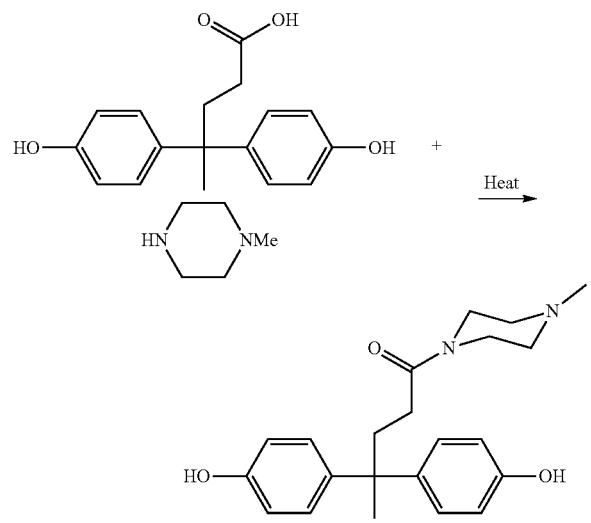

This is contrast to the "two-step method" described in U.S. Pat. No. 7,985,339 assigned to General Electric Company.

The method includes contacting diphenolic acid with N-methyl piperazine to form a reaction mixture. In some embodiments, a molar ratio of N-methyl piperazine to diphenolic acid is in a range from about 1.5 to about 5. In some embodiments, a molar ratio of N-methyl piperazine to diphenolic acid is in a range from about 3 to about 5. In certain embodiments, a molar ratio of N-methyl piperazine to diphenolic acid is in a range from about 3 to about 4.

The diphenolic acid is contacted with N-methyl piperazine under substantially solvent-free conditions, in some embodiments. The term "substantially solvent-free conditions" as used herein means the amount of solvent added during the step of contacting the diphenolic acid with N-methyl piperazine is less than about 10 weight percent of the total reaction mixture. In certain embodiments, the reaction mixture is formed without adding any solvent to the mixture, and the reaction mixture may be completely solvent free. In some embodiments, the reaction mixture may be in the form of a slurry, formed by adding solid diphenolic acid to a solution of N-methyl piperazine.

As alluded to previously, in a typical two-step method, large quantities of a solvent (e.g., methanol) are typically used during the step of converting the diphenolic acid to corresponding ester, which requires an additional step of solvent removal and may be cost-prohibitive. In contrast, the method in accordance with some embodiments of the invention precludes the need to add a solvent, and may therefore be more cost-effective. Further, the one-step method may be more efficient and may provide higher yields when compared to two-step method, which requires an additional isolation and purification step.

The method further includes heating the reaction mixture to form a reaction product including N-methyl piperazine diphenolamide. In some embodiments, the method includes heating the reaction mixture at a temperature in a range from about 140° C. to about 180° C. for time duration in a range from about 8 hours to about 40 hours. In some embodiments, the method includes heating the reaction mixture at a temperature in a range from about 160° C. to about 180° C. for time duration in a range from about 16 hours to about 40 hours. In some embodiments, the reaction mixture may be heated to the desired temperature in a step-wise manner over a period of time. The reaction product may be in the form of a solution or a slurry, in some embodiments.

The method further includes isolating the N-methyl piperazine diphenolamide from the reaction product. In certain embodiments, the N-methyl piperazine diphenolamide is isolated from the reaction product by crystallization from a suitable solvent.

The reaction product may be substantially free of diphenolic acid methyl ester. The term "substantially free" as used herein means that the amount of diphenolic acid methyl ester in the reaction product is less than 0.1 weight percent. In some embodiments, the reaction product is completely free of diphenolic acid methyl ester, that is, the amount of diphenolic acid methyl ester in the reaction product is 0 weight percent.

The isolated N-methyl piperazine diphenolamide may have purity greater than about 96% in some embodiments. In certain embodiments, the isolated N-methyl piperazine diphenolamide may have purity greater than about 98%. Further, a yield of N-methyl piperazine diphenolamide relative to diphenolic acid may be greater than about 80%. In certain embodiments, a yield of N-methyl piperazine diphenolamide relative to diphenolic acid may be greater than about 85%.

In some embodiments, a method for synthesis of N-methyl piperazine diphenolamide includes contacting diphenolic acid with N-methyl piperazine under substantially solvent free conditions to form a reaction mixture; and heating the reaction mixture at a temperature in a range from about 160° C. to about 180° C. for a time duration in a range from about 16 hours to about 40 hours, to form a reaction product including the N-methyl piperazine diphenolamide.

A composition including N-methyl piperazine diphenolamide is also presented. The composition is formed by contacting diphenolic acid with N-methyl piperazine to form a reaction mixture; and heating the reaction mixture to form a reaction product comprising the N-methyl piperazine diphenolamide. As alluded to previously, the composition is substantially free of diphenolic acid methyl ester in some embodiments. Further, the N-methyl piperazine diphenolamide has purity greater than about 98%.

EXAMPLES

Chemicals were purchased from Aldrich and used as received, unless otherwise noted.

Example 1

Preparation of N-Methyl Piperazine Diphenolamide (N-MePip DPA) by One-Step Method A 1.0 liter three neck flask equipped with reflux condenser and overhead mechanical stirrer was charged with 400 grams (4.0 moles) of N-methyl piperazine. The resulting solution was stirred at room temperature under nitrogen. To this solution was added 286 grams (1.00 mole) of diphenolic acid as a solid over 10 minutes to ensure no solid caking and a homogeneous mixture. The resulting slurry was heated with an external oil bath temp of 160° C., and during the course of heating, the slurry became a clear solution, which began to re-precipitate as the oil temperature approached 80° C. (ammonium salt formation). As the oil temperature continued to rise to 110° C., the reaction mixture became a thick paste, which gradually thinned out and re-melted as the oil bath temp approached 160° C. The temperature was maintained at 160° C. for 8 hours during which time the reaction mixture became a clear, amber liquid. Further, during this time the internal pot temperature rose from 125° C. to 136° C. After 8 hours, the oil temperature was gradually raised to 180° C., and this oil bath temperature was maintained until all the starting material was gone (~additional 8-16 hours). Excess N-methyl piperazine was allowed to distill off over the course of the reaction (total distilled N-methyl piperazine was ~15 grams). It was determined that it was desirable not to distill more than 20 grams or the reaction risked crystallization upon cooling. Over the course of the reaction, the pot temperature increased from 125° C. to 148° C.

Upon completion, as determined by HPLC, the mixture was cooled to ~110° C. (internal temperature), and 1.0 L of water was added slowly to maintain a solution. Initially, the water was added at the rate of 2.0 mL/min for the first 100 mL of added water, during which time the amber solution became less viscous, and further began to precipitate as a white solid (the internal temperature dropped to ~86° C.). The remaining water was added over 1 hour (at the rate of 15 mL/min) After all the water was added, the temperature was allowed to cool to room temperature, resulting in a slurry containing a white precipitate. The precipitate was obtained by filtration to obtain an off white solid. The crude solid was dried by heating gradually from 50° C. to 80° C. under vacuum over 24 hours (95% isolated yield, ~99% purity).

The resulting dried solid was dissolved in hot ethanol (1.0 liter) to which 500 ml of water was added slowly while maintaining temperature at 80° C. Upon addition of all the water the heat was removed and the solution allowed to cool to room temperature and stirred for additional 12 hours. The recrystallized product was isolated by filtration and dried under vacuum at 50° C. to 80° C. over a period of 24 hours. 312.8 g of a pure white solid was obtained in 85% yield with greater than 99% purity, m.p. 196-197° C.

Comparative Example 1

Preparation of N-Methyl Piperazine Diphenolamide (N-MePip DPA) by Two-Step Method N-methyl piperazine diphenolamide was also synthesized using a two-step method from the corresponding methyl ester, as described in U.S. Pat. No. 7,985,339 assigned to General Electric Company. The two-step method resulted in 80-85% isolated yield of crude material by precipitation with acetone-water mixture. Therefore, the crude overall yield from this two-step method was less than the crude yield from the one-step method described in Example 1.

The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied; those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:

1. A method for synthesis of N-methyl piperazine diphenolamide, comprising:
   contacting diphenolic acid with N-methyl piperazine to form a reaction mixture; and heating the reaction mixture to form a reaction product comprising N-methyl piperazine diphenolamide.

2. The method of claim 1, wherein diphenolic acid is contacted with N-methyl piperazine under substantially solvent-free conditions.

3. The method of claim 1, wherein a molar ratio of N-methyl piperazine to diphenolic acid is in a range from about 1.5 to about 5.

4. The method of claim 1, wherein a molar ratio of N-methyl piperazine to diphenolic acid is in a range from about 3 to about 4.

5. The method of claim 1, comprising heating the reaction mixture at a temperature in a range from about 140° C. to about 180° C. for a time duration in a range from about 8 hours to about 40 hours.

6. The method of claim 1, comprising heating the reaction mixture at a temperature in a range from about 160° C. to about 180° C. for a time duration in a range from about 16 hours to about 24 hours.

7. The method of claim 1, further comprising isolating N-methyl piperazine diphenolamide from the reaction product by crystallization.

8. The method of claim 1, wherein N-methyl piperazine diphenolamide has a purity greater than about 98%.

9. The method of claim 1, wherein the reaction product is substantially free of diphenolic acid methyl ester.

10. The method of claim 1, wherein a yield of N-methyl piperazine diphenolamide relative to diphenolic acid is greater than about 80%.

11. A method for synthesis of N-methyl piperazine diphenolamide, comprising:
    contacting diphenolic acid with N-methyl piperazine under substantially solvent free conditions to form a reaction mixture; and
    heating the reaction mixture at a temperature in a range from about 160° C. to about 180° C. for a time duration in a range from about 16 hours to about 24 hours, to form a reaction product comprising N-methyl piperazine diphenolamide.

12. The method of claim 11, wherein a molar ratio of N-methyl piperazine to diphenolic acid is in a range from about 1.5 to about 5.

13. The method of claim 11, wherein a molar ratio of N-methyl piperazine to diphenolic acid is in a range from about 3 to about 4.

14. A composition comprising N-methyl piperazine diphenolamide, formed by:
    contacting diphenolic acid with N-methyl piperazine to form a reaction mixture; and heating the reaction mixture to form a reaction product comprising the N-methyl piperazine diphenolamide.

15. The composition of claim 14, wherein the composition is substantially free of diphenolic acid methyl ester.

16. The composition of claim 14, wherein N-methyl piperazine diphenolamide has a purity greater than about 98%.

17. The composition of claim 14, formed by contacting about 1.5 moles to about 5 moles of N-methyl piperazine relative to 1 mole of diphenolic acid.

18. The composition of claim 14, formed by contacting about 3 moles to about 4 moles of N-methyl piperazine relative to 1 mole of diphenolic acid.

19. The composition of claim 14, formed by heating the reaction mixture at a temperature in a range from about 140° C. to about 180° C. for a time duration in a range from about 8 hours to about 40 hours.

20. The composition of claim 14, formed by heating the reaction mixture at a temperature in a range from about 160° C. to about 180° C. for a time duration in a range from about 16 hours to about 24 hours.

* * * * *